United States Patent
Wei et al.

(10) Patent No.: US 8,833,941 B2
(45) Date of Patent: Sep. 16, 2014

(54) DIGITAL SLIT-LAMP MICROSCOPE SYSTEM AND METHOD OF ELECTRONIC RECORD AND REMOTE DIAGNOSIS

(71) Applicant: Shanghai Mediworks Precision Instruments Co. Ltd, Shanghai (CN)

(72) Inventors: Yue Wei, Shanghai (CN); Wenguang Chen, Shanghai (CN); Sufeng Yan, Shanghai (CN); Yunxiao Han, Shanghai (CN); Shaojuan Wang, Shanghai (CN); Xianran Peng, Shanghai (CN); Hang Yu, Shanghai (CN); Zhaosong Kong, Shanghai (CN)

(73) Assignee: Shanghai Mediworks Precision Instruments Co. Ltd, Shanghai (CN)

( * ) Notice: Subject to any disclaimer, the term of this patent is extended or adjusted under 35 U.S.C. 154(b) by 0 days.

(21) Appl. No.: 13/866,356

(22) Filed: Apr. 19, 2013

(65) Prior Publication Data
US 2013/0229625 A1    Sep. 5, 2013

Related U.S. Application Data

(63) Continuation of application No. PCT/CN2012/073802, filed on Apr. 11, 2011.

(30) Foreign Application Priority Data

Apr. 11, 2011 (CN) .......................... 2011 1 0089269

(51) Int. Cl.
| | | |
|---|---|---|
| *A61B 3/10* | (2006.01) |
| *A61B 3/14* | (2006.01) |
| *A61B 3/00* | (2006.01) |
| *A61B 3/117* | (2006.01) |
| *A61B 3/135* | (2006.01) |

(52) U.S. Cl.
CPC .................. *A61B 3/117* (2013.01); *A61B 3/135* (2013.01)
USPC ........... 351/214; 351/205; 351/210; 351/221; 351/245

(58) Field of Classification Search
USPC .......................... 351/205, 210, 214, 221, 245
See application file for complete search history.

(56) References Cited

U.S. PATENT DOCUMENTS

| | | | |
|---|---|---|---|
| 5,912,720 A | | 6/1999 | Berger et al. |
| 6,013,034 A | * | 1/2000 | Fernandes Da Cunha Vaz et al. ..... 600/476 |
| 2003/0035084 A1 | | 2/2003 | Makino |
| 2003/0117580 A1 | | 6/2003 | Franz et al. |
| 2004/0135971 A1 | | 7/2004 | Ulbers |
| 2010/0152847 A1 | * | 6/2010 | Padrick et al. ................ 623/6.11 |

* cited by examiner

FOREIGN PATENT DOCUMENTS

| | | |
|---|---|---|
| CN | 1448107 | 10/2003 |
| CN | 101729780 | 6/2010 |

*Primary Examiner* — Scott J Sugarman
*Assistant Examiner* — Mustak Choudhury
(74) *Attorney, Agent, or Firm* — Woodard, Emhardt, Moriarty, McNett & Henry LLP

(57) ABSTRACT

The present patent application discloses a digital slit-lamp microscope system and the methods of the electronic recording and remote diagnosis. The present patent application relates to the field of optical instrument and remote communication control. The purpose is to solve the problems of the electronic recording, reappearing and remote diagnosis of the slit-lamp image. The digital slit-lamp microscope system comprises digital slit-lamp microscope side, communication unit and client side. The digital slit-lamp microscope side includes a build-in slit-lamp microscope and is connected to the communication unit and the client side in sequence. The digital slit-lamp microscope side irradiates the eyes of the patient, and then transmits the pathology information of the eyes of the patient to the communication unit and the client side in sequence.

14 Claims, 1 Drawing Sheet

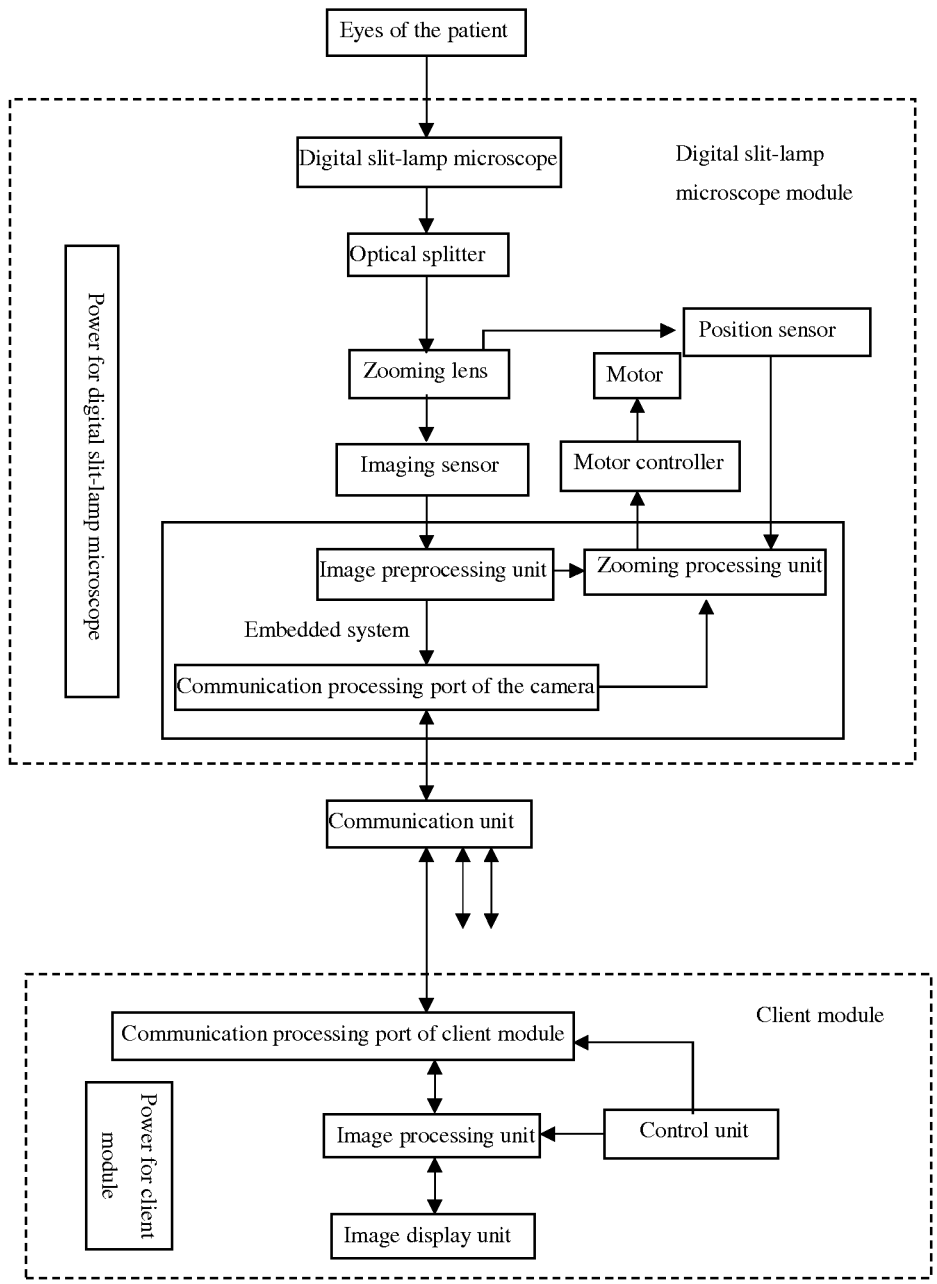

DIGITAL SLIT-LAMP MICROSCOPE SYSTEM AND METHOD OF ELECTRONIC RECORD AND REMOTE DIAGNOSIS

FIELD OF TECHNOLOGY

The present patent application relates to the field of optical instrument, and particularly relates to a digital slit-lamp microscope system and methods of electronic record and remote diagnosis.

BACKGROUND

The existing slit-lamp microscope system is generally used for diagnosing anterior segment of eyes. It is an imaging and diagnosing equipment by narrow light beam used in the ophthalmology department. The eyepiece is generally used to output information of pathological changes of a patient's eyes. The patient must be checked on site by a doctor. The information of the pathological changes must be written in the medical record by the doctor. The information of the nidus part cannot be recorded exactly of the time. The records are restricted to the doctor's observation and understanding of the patient's conditions. The information of the pathological changes cannot be enlarged and checked on monitor. The check is restricted to the resolution ratio of the doctor's naked eye. If another doctor wants to know the conditions, he/she needs to recheck.

The doctor cannot display or store the conditions of the nidus part of the patient through the computer. He/she cannot record the conditions and print out for the patient to take away.

The patient's conditions cannot be transmitted to an expert in another place to diagnose. The expert in another place cannot remotely control the digital slit-lamp microscope to check different parts of eyes of the patient in different ways.

At present, there is still not a slit-lamp microscope system in the market which can overcome the above-mentioned defects.

SUMMARY

In order to solve the problems of the existing technology, the present patent application provides a digital slit-lamp microscope system and methods of electronic record and remote diagnosis. The information checked by the slit-lamp microscope in ophthalmology can be achieved by electronic record. The information is transferred to the internet through communication interface finally. The remote diagnosis and remote driving can be achieved. Thus the ophthalmic checking can be performed while not on site and remote expert consultation is achieved.

According to one aspect of the present patent application, a digital slit-lamp microscope system includes: a digital slit-lamp microscope side, which includes a build-in slit-lamp microscope, a communication unit and a client side. The digital slit-lamp microscope side, the communication unit and the client side are connected in sequence.

The digital slit-lamp microscope includes optical splitter, zooming lens and imaging sensor. The zooming lens is coupled to the digital slit-lamp microscope via the optical splitter and images in the imaging sensor. The imaging sensor is coupled to the communication unit. The imaging sensor is coupled to communication processing port of the camera side via an image preprocessing unit. The communication processing port of the camera side is connected to the communication unit.

The image preprocessing unit is coupled to the zooming lens via a zooming processing unit a motor controller and a motor in sequence. The zooming lens is coupled to the zooming processing unit via a position sensor. The communication processing port of the camera side is connected to the zooming processing unit.

The image preprocessing unit, the communication processing port of the camera side and the zooming processing unit are combined into an embedded system. According to another aspect of the present patent application, a method of electronic record and remote diagnosis includes at least the following steps: the slit-lamp microscope emits light to the eyes of the patient and collects the light reflecting back from the eyes of the patient as the optical information of the eyes of the patient, the digital slit-lamp microscope side transfers the signal of the optical information to the client side through the communication unit, the client side remotely records, reproduces or processes pathology information of the eyes of the patient in form of images, the client side remotely controls the digital silt-lamp microscope side by the communication unit to collect the optical information of the eyes of the patient.

The digital slit-lamp microscope side transfers the signal of the optical information to the client side through the communication unit by the following ways: the zooming lens receive the optical information of the eyes of the patient collected by the slit-lamp microscope by the optical splitter, the imaging sensor converts the optical information of the eyes of the patient received by the zooming lens into electrical signal, the imaging sensor is coupled to the communication unit via the image preprocessing unit, the communication processing port of the camera side in sequence in order to transfer the electrical signal of the imaging sensor to the communication unit, the communication unit transfers the electrical signal to the client side.

The image preprocessing unit is connected to the zooming processing unit. The zooming processing unit, the motor controller, the motor and the zooming lens are connected in sequence. The action of the zooming lens is controlled according to the electrical signal transferred from the imaging sensor and the optical information of the eyes of the patient is collected.

The communication processing port of the camera side and the zooming processing unit are interconnected. The zooming processing unit, the motor controller, the motor and the zooming lens are connected in sequence. The action of the zooming lens is controlled according to the control information of the client side transferred from the communication unit and the optical information of the eyes of the patient is collected.

The zooming lens drives the position sensor. The position sensor feedbacks the action information of the zooming lens to the zooming processing unit to control the motor accurately.

The client side includes a communication processing port of the client side, an image processing unit, an image display unit and a control unit. The communication processing port of the client side, the image processing unit and the image display unit are connected in sequence. The communication processing port of the client side and the image processing unit convert the communication signal transferred from the communication unit into image signal, and then the image signal is displayed by the image display unit. The image processing unit records and compiles the image signal. The control unit is connected to and controls the image processing unit. The control unit controls the reproduce, record and processing of the image signal. The control unit controls the zooming unit to zoom at different parts of the eyes of the patient and collects the light signal by the image processing unit the communication processing port of the client side, the communication unit, the communication processing port of the camera side, the motor controller and the motor. The control unit is connected to and controls the communication processing port of the client to process the information from the communication unit.

A power supply of the client side or the image processing unit can provide power to the control unit.

The communication unit can be a telecommunication cable, optical cable, local area network or internet.

In one embodiment, the client side can be a remote computer.

The present patent application has below advantages:

The information checked by the slit-lamp microscope in ophthalmology is linked into the internet through communication interface finally. The remote diagnosis and remote drive can be achieved. Thus the ophthalmic checking can be performed while not on site and remote expert consultation is achieved.

The doctor can window and enlarge the image at the client side. The doctor can use a mouse to select and enlarge the area that needs to be checked specially. They can enlarge the areas where more details need to be known and thus the quality of checking is enhanced.

Compared to the traditional fixed-focus ophthalmic inspection equipment the digital slit-lamp microscope system can adjust the focal distance by the mouse wheel and zoom at the organizations of parts at different levels of the eyeball selectively.

Compared to the traditional slit-lamp checking, the digital slit-lamp microscope system can save and print the inspection result by software. The medical record of the patient can be stored and reproduced conveniently.

The eyepiece output mode and the joint output mode by the eyepiece and digital image can be switched. It is more convenient for the doctor to use.

It is more convenient to assemble, debug and acquire better imaging quality.

BRIEF DESCRIPTION OF THE DRAWINGS

FIG. 1 is a structure schematic diagram of the present patent application, which shows: eyes of the patient, a digital slit-lamp microscope side, a slit-lamp microscope, zooming lens, an imaging sensor, an image preprocessing unit, a communication processing port of the camera side, a zooming processing unit, a motor, a motor controller, a position sensor, a power supply of the digital slit-lamp microscope side, a communication unit, a client side, a communication processing port of the client side, an image processing unit, an image display unit, a control unit and a power supply of the client side.

DETAILED DESCRIPTION

The principles of the present patent application will be further described with reference to the drawings.

As show in FIG. 1, a digital slit-lamp microscope system and methods of electronic record and remote diagnosis of the present patent application are used to diagnose the eyes of the patient. The digital slit-lamp microscope system includes a digital slit-lamp microscope side which has a build-in slit-lamp microscope. The slit-lamp microscope emits light to eyes of a patient and collects the light reflecting back from the eyes of the patient as pathology information. The digital slit-lamp microscope system also includes a communication unit and at least one client side. The digital slit-lamp microscope side, the communication unit and the client side are connected in sequence and transfer the pathology information of the eyes of the patient. The client side remotely records, reproduces or processes the pathology information of the eyes of the patient in form of images. The client side can remotely control the digital slit-lamp microscope side by the communication unit to collect optical information of the eyes of the patient.

The digital slit-lamp microscope side further includes an optical splitter, zooming lens, a imaging sensor, an image preprocessing unit, a communication processing port of the camera side, a zooming processing unit, a motor controller, a motor, a position sensor, a power supply of the digital slit-lamp microscope side.

The zooming lens collects light of the eyes of the patient received by the slit-lamp microscope through the optical splitter.

The imaging sensor converts the optical information received by the zooming lens into electrical signal.

The imaging sensor is connected to the image preprocessing unit. The image preprocessing unit, the communication processing port of the camera side and the communication unit are connected in sequence in order to transfer the electrical signal of the imaging sensor to the communication unit.

The image preprocessing unit is connected to the zooming processing unit. The communication processing port of the camera side and the zooming processing unit are interconnected. The zooming processing unit, the motor controller, the motor and the zooming lens are connected in sequence. The action of the zooming lens is controlled according to the control information of the client side transferred from the communication unit and the optical information of the eyes of the patient is collected.

The zooming lens drives the position sensor. The position sensor feedbacks the action information of the zooming lens to the zooming processing unit to control the motor accurately.

The power supply of the digital slit-lamp microscope side provides power to all or part of the light source of the slit-lamp microscope, the position sensor of the zooming lens, the imaging sensor, the image preprocessing unit, the zooming processing unit, the motor controller, the communication processing port of the camera side and the communication unit.

The image preprocessing unit, the communication processing port of the camera side and the zooming processing unit are combined into an embedded system.

The client side includes a communication processing port of the client side, an image processing unit, an image display unit, a control unit, and a power supply of the client side.

The communication processing port of the client side, the image processing unit and the image display unit are connected in sequence. The communication processing port of the client side and the image processing unit convert the communication signal transferred from the communication unit into linage signal. Then the image signal is displayed by the image display unit. The image processing unit records and compiles the image signal.

The control unit can be a mouse, keyboard, operating handle or any combination thereof.

The power supply of the client side can provide power to all or part of the communication unit, the communication processing port of the client side, the image processing unit and the image display unit.

The control unit is connected to and controls the image processing unit. The control unit controls the reproduce, record and processing of the image signal. The control unit controls the zooming unit to zoom at different pans of the eyes of the patient and collects the light signal by the image processing unit, the communication processing port of the client side, the communication unit, the communication processing port of the camera side, the motor controller and the motor.

The control unit is connected to and controls the communication processing port of the client side to process the information from the communication unit.

The power supply of the client side or the image processing unit can provide power to the control unit.

The communication unit can be a telecommunication cable, optical cable, local area network or internet.

In one embodiment, the client side can be a remote computer.

When the digital slit-lamp microscope system of this embodiment is in operating, the slit light source of the digital slit-lamp microscope irradiates the eyes of the patient. The reflected light enters into the microscope system of the digital slit-lamp microscope and is split into two light beams. One of the light beams images in the optoelectronic coupling imaging sensor via the zooming lens. The image signal collected and preprocessed by the digital imaging system of the image preprocessing unit is transferred to the zooming processing unit and the communication processing port of the camera side simultaneously.

The communication processing port is connected to the local area network or the internet and provides HTTP (Hyper Text Transport Protocol) control service and real-time image service to the client side. The client side is connected to the digital slit-lamp microscope side by the local area network or the internet. The client side receives and displays the real-time image data, and remotely control the digital slit-lamp microscope side via the HTTP control service.

The user can observe the images taken by the digital slit-lamp microscope side from the monitor connected to the client side computer and control the software by the mouse and keyboard connected to the computer. The client side computer can send a control instruction to the communication processing port of the camera side via the communication unit. The image processing unit of the camera side sends the control instruction to the zooming processing unit. And then the zooming processing unit drives the motor controller to zoom according to the signal transferred from the position sensor, so that the imaging sensor can acquire the image signal which is needed.

What is claimed is:

1. A digital slit-lamp microscope system comprising:
   a digital slit-lamp microscope module;
   a communication unit; and
   a remote client module,
   wherein the communication unit is a telecommunication cable or optical cable or local area network or internet;
   the digital slit-lamp microscope module and the client module are connected by the telecommunication cable or optical cable or local area network or internet;
   wherein the digital slit-lamp microscope module comprises a build-in slit-lamp microscope, an optical splitter, zooming lens and an imaging sensor; the zooming lens is coupled to the digital slit-lamp microscope via the optical splitter and images in the imaging sensor, the imaging sensor is coupled to the communication unit, the imaging sensor is coupled to a communication processing port of the microscope module via an image preprocessing unit, the communication processing port of the microscope module is connected to the communication unit; wherein the image preprocessing unit is coupled to the zooming lens via a zooming processing unit, a motor controller and a motor in sequence, the zooming lens is coupled to the zooming processing unit via a position sensor, the communication processing port of the microscope module is connected to the zooming processing unit; and
   wherein the client module remotely operates the digital slit-lamp microscope module by the communication unit to collect optical information of eyes of a patient; the client module remotely records, reproduces or processes pathology information of the eyes of the patient in form of images.

2. The digital slit-lamp microscope system in claim 1, wherein the image preprocessing unit, the communication processing port of the microscope module, the zooming processing unit are combined into an embedded system.

3. A method of electronic record and remote diagnosis using the system in claim 1, comprises at least the following steps:
   A) emitting light to eyes of a patient and collecting the light reflecting back from the eyes of the patient as optical information of the eyes of the patient by the slit-lamp microscope;
   B) transferring the information to a remote client module by the digital slit-lamp microscope to the client module through the communication unit;
   C) recording, reproducing or processing the information in form of images by the client module remotely; and
   D) controlling the digital slit-lamp microscope module by the communication unit to collect the optical information of the eyes of the patient by the client module remotely.

4. The method of electronic record and remote diagnosis in claim 3, wherein the step B) further comprising the steps of:
   receiving the optical information of the eyes of the patient collected by the slit-lamp microscope by the optical splitter by the zooming lens,
   converting the optical information of the eyes of the patient received by the zooming lens into electrical signal by an imaging sensor, the imaging sensor is coupled to the communication unit via a image preprocessing unit, a communication processing port of the microscope module in sequence;
   transferring the electrical signal of the imaging sensor to the communication unit; and
   transferring the electrical signal to the client module by the communication unit.

5. The method of electronic record and remote diagnosis in claim 4, wherein the image preprocessing unit is connected to a zooming processing unit, the zooming processing unit, the motor controller, the motor and the zooming lens are connected in sequence, the action of the zooming lens is controlled according to the electrical signal transferred from the imaging sensor and the optical information of the eyes of the patient is collected.

6. The method of electronic record and remote diagnosis in claim 5, wherein the zooming lens drives the position sensor, the position sensor feedbacks the action information of the zooming lens to the zooming processing unit to control the motor accurately.

7. The method of electronic record and remote diagnosis in claim 4, wherein the communication processing port of the microscope module and the zooming processing unit are interconnected, the zooming processing unit, the motor controller, the motor and the zooming lens are connected in sequence, the action of the zooming lens is controlled according to the control information of the client module transferred from the communication unit and the optical information of the eyes of the patient is collected.

8. The method of electronic record and remote diagnosis in claim 7, wherein the zooming lens drives the position sensor, the position sensor feedbacks the action information of the zooming lens to the zooming processing unit to control the motor accurately.

9. The method of electronic record and remote diagnosis in claim 4, wherein the client module comprises a communication processing port of the client module, an image processing unit, an image display unit and a control unit, the communication processing port of the client module, the image processing unit and the image display unit are connected in sequence, the communication processing port of the client module and the image processing unit convert the communication signal transferred from the communication unit into image signal, and then the image signal is displayed by the image display unit, the image processing unit records and compiles the image signal, the control unit is connected to and controls the image processing unit, the control unit controls the reproduce, record and processing of the image signal, the control unit controls the zooming unit to zoom at different parts of the eyes of the patient and collects light signal by the image processing unit, the communication processing port of the client module, the communication unit, the communication processing port of the microscope module, the motor controller and the motor, the control unit is connected to and controls the communication dispose port of the client to process the information from the communication unit.

10. The method of electronic record and remote diagnosis in claim 3, wherein the client module comprises a communication processing port of the client module, an image processing unit, an image display unit and a control unit, the communication processing port of the client module, the image processing unit and the image display unit are connected in sequence, the communication processing port of the client module and the image processing unit convert the communication signal transferred from the communication unit into image signal, and then the image signal is displayed by the image display unit, the image processing unit records and compiles the image signal, the control unit is connected to and controls the image processing unit, the control unit controls the reproduce, record and processing of the image signal, the control unit controls the zooming unit to zoom at different parts of the eyes of the patient and collects light signal by the image processing unit, the communication processing port of the client module, the communication unit, the communication processing port of the microscope module, the motor controller and the motor, the control unit is connected to and controls the communication dispose port of the client to process the information from the communication unit.

11. A digital slit-lamp microscope system comprising:
a digital slit-lamp microscope module, which comprises a build-in slit-lamp microscope;
a communication unit; and
a remote client module,
wherein the communication unit is a telecommunication cable, or optical cable, or local area network or internet;
the digital slit-lamp microscope module and the client module are connected in sequence by the telecommunication cable, or optical cable, or local area network or internet;
wherein the digital slit-lamp microscope module comprises a build-in slit-lamp microscope, an optical splitter, zooming lens and an imaging sensor; the zooming lens is coupled to the digital slit-lamp microscope via the optical splitter and images in the imaging sensor, the imaging sensor is coupled to the communication unit, the imaging sensor is coupled to a communication processing port of the microscope module via an image preprocessing unit, the communication processing port of the microscope module is connected to the communication unit; and
wherein the client module remotely operates the digital slit-lamp microscope module by the communication unit to collect optical information of eyes of a patient; the client module remotely records, reproduces or processes pathology information of the eyes of the patient in form of images.

12. The digital slit-lamp microscope system in claim 11, wherein the client module comprises a communication processing port of the client module, an image processing unit, an image display unit and a control unit; the communication processing port of the client module, the image processing unit and the image display unit are connected in sequence; the communication processing port of the client module and the image processing unit convert the communication signal transferred from the communication unit into image signal, and then the image signal is displayed by the image display unit; the image processing unit records and compiles the image signal; the control unit is connected to and controls the image processing unit; the control unit controls reproducing, recording and processing of the image signal; the control unit controls the zooming unit to zoom at different parts of the eyes of the patient and collects the light signal by the image processing unit, the communication processing port of the client module, the communication unit, the communication processing port of the microscope side, the motor controller and the motor; the control unit is connected to and controls the communication processing port of the client to process the information from the communication unit.

13. The digital slit-lamp microscope system in claim 12, wherein the image preprocessing unit is coupled to the zooming lens via a zooming processing unit, a motor controller and a motor in sequence, the zooming lens is coupled to the zooming processing unit via a position sensor, the communication processing port of the microscope module is connected to the zooming processing unit.

14. The digital slit-lamp microscope system in claim 13, wherein the image preprocessing unit, the communication processing port of the microscope module, the zooming processing unit are combined into an embedded system.

* * * * *